United States Patent
Cheng et al.

(10) Patent No.: US 7,273,492 B2
(45) Date of Patent: Sep. 25, 2007

(54) STENT FOR TREATING VULNERABLE PLAQUE

(75) Inventors: E Tina Cheng, Union City, CA (US); Daniel L. Cox, Palo Alto, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 10/462,984

(22) Filed: Jun. 17, 2003

(65) Prior Publication Data

US 2004/0044400 A1    Mar. 4, 2004

Related U.S. Application Data

(63) Continuation of application No. 10/228,850, filed on Aug. 27, 2002, now abandoned.

(51) Int. Cl.
     *A61F 2/06*      (2006.01)
(52) U.S. Cl. ..................... 623/1.11; 623/1.15
(58) Field of Classification Search ............... 623/1.15, 623/1.11
See application file for complete search history.

(56) References Cited

U.S. PATENT DOCUMENTS

| | | | |
|---|---|---|---|
| 5,817,126 A * | 10/1998 | Imran | 606/198 |
| 5,924,997 A | 7/1999 | Campbell | |
| 6,245,026 B1 | 6/2001 | Campbell et al. | |
| 6,273,910 B1 * | 8/2001 | Limon | 623/1.15 |
| 6,273,911 B1 * | 8/2001 | Cox et al. | 623/1.15 |
| 6,383,171 B1 * | 5/2002 | Gifford et al. | 604/508 |
| 6,450,971 B1 | 9/2002 | Andrus et al. | |
| 6,451,044 B1 | 9/2002 | Naghavi et al. | |
| 6,602,246 B1 * | 8/2003 | Joye et al. | 606/21 |
| 2001/0047138 A1 | 11/2001 | Kokate et al. | |
| 2002/0009535 A1 | 1/2002 | Michal et al. | |
| 2002/0062147 A1 | 5/2002 | Yang | |
| 2002/0077564 A1 | 6/2002 | Campbell et al. | |
| 2002/0082515 A1 | 6/2002 | Campbell et al. | |
| 2002/0091436 A1 | 7/2002 | Phelps et al. | |
| 2003/0125799 A1 * | 7/2003 | Limon | 623/1.15 |

* cited by examiner

*Primary Examiner*—Corrine McDermott
*Assistant Examiner*—Christopher D. Prone
(74) *Attorney, Agent, or Firm*—Fulwider Patton LLP

(57) ABSTRACT

An intravascular stent assembly for implantation in a body lumen, such as a coronary artery, is designed to treat a lesion with vulnerable plaque by reducing the fibrous cap stresses. The stent includes distal, proximal, and center sections where the center section is configured to treat the vulnerable plaque. The stent consists of radially expandable cylindrical rings generally aligned on a common longitudinal stent axis and either directly connected or interconnected by one or more interconnecting links placed so that the stent is flexible in the longitudinal direction while providing high degrees of radial strength and vessel scaffolding.

10 Claims, 11 Drawing Sheets

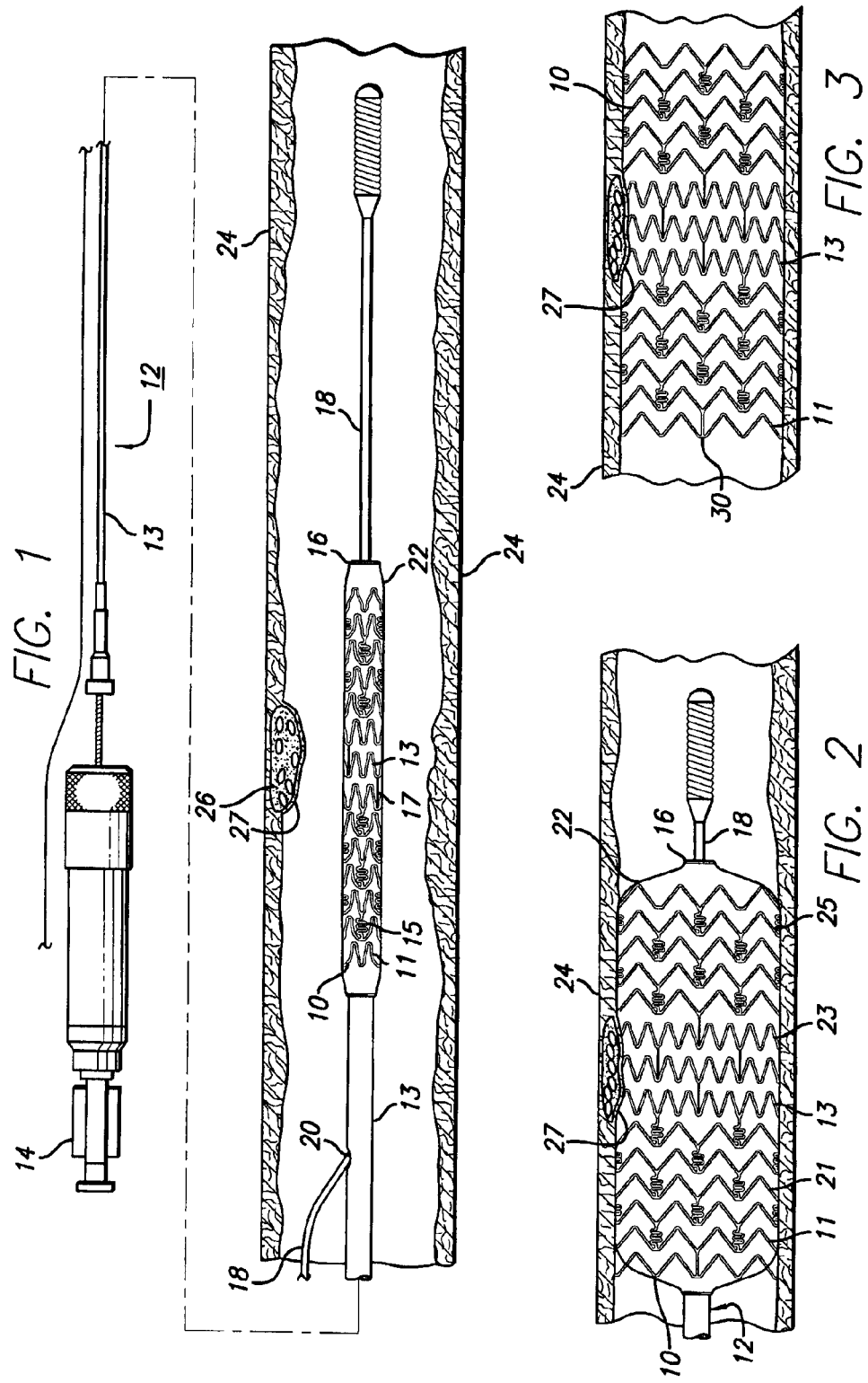

STENT FOR TREATING VULNERABLE PLAQUE

The present application is a continuation of application Ser. No. 10/228,850 filed Aug. 27, 2002 now abandoned.

BACKGROUND OF THE INVENTION

The present invention relates to vascular repair devices, and in particular to intravascular stents, which are adapted to be implanted into a patient's body lumen, such as a blood vessel or coronary artery, for the treatment of unstable or vulnerable, human atherosclerotic plaque.

Currently, the treatment of unstable or vulnerable plaque presents a significant therapeutic challenge to medical investigators. Vulnerable plaque is characterized by a basic lesion which is a raised plaque beneath the innermost arterial layer, the intima. Atherosclerotic plaques are primarily composed of varying amounts of long chain extracellular matrix (ECM) proteins that are synthesized by smooth muscle cells. The other primary lesion component of atherosclerotic plaque includes lipoproteins, existing both extracellularly and within foam cells derived primarily from lipid-laden macrophages. In a more advanced lesion, a necrotic core may develop, consisting of lipids, foam cells, cell debris, and cholesterol crystals, and myxomatous configurations with crystalline lipid forms. The necrotic core is rich in tissue factor and quite thrombogenic, but in the stable plaque it is protected from the luminal blood flow by a robust fibrous cap composed primarily of long chain ECM proteins, such as elastin and collagen, which maintain the strength of the fibrous cap. The aforementioned plaque represents the most common form of vulnerable plaque, known as a fibroatheroma. Histology studies from autopsy suggest this form constitutes the majority of vulnerable plaques in humans. A second form of vulnerable plaque represents a smaller fraction of the total, and these are known as erosive plaques. Erosive plaques generally have a smaller content of lipid, a larger fibrous tissue content, and varying concentrations of proteoglycans. Various morphologic features that have been associated with vulnerable plaque, include thinned or eroded fibrous caps or luminal surfaces, lesion eccentricity, proximity of constituents having very different structural moduli, and the consistency and distribution of lipid accumulations. With the rupture of fibroatheroma forms of vulnerable plaque, the luminal blood becomes exposed to tissue factor, a highly thrombogenic core material, which can result in total thrombotic occlusion of the artery. In the erosive form of vulnerable plaque, mechanisms of thrombosis are less understood but may still yield total thrombotic occlusion.

Although rupture of the fibrous cap in a fibroatheroma is a major cause of myocardial infarction (MI) related deaths, there are currently no therapeutic strategies in place to treat lesions that could lead to acute MI. The ability to detect vulnerable plaques and to treat them successfully with interventional techniques before acute MI occurs has long been an elusive goal. Numerous finite element analysis (FEA) studies have proved that, in the presence of a soft lipid core, the fibrous cap shows regions of high stresses. Representative of these studies include the following research articles, each of which are incorporated in their entirety by reference herein: Richardson et al. (1989), Influence of Plaque Configuration and Stress Distribution on Fissuring of Coronary Atherosclerotic Plaques, Lancet, 2(8669), 941–944; Loree et al. (1992), Effects of Fibrous Cap Thickness on Circumferential Stress in Model Atherosclerotic Vessels, Circulation Research, 71, 850–858; Cheng et al. (1992), Distribution of Circumferential Stress in Ruptured and Stable Atherosclerotic Lesions: A Structural Analysis With Histopathological Correlation, Circulation, 87,1179–1187; Veress et al. (1993), Finite Element Modeling of Atherosclerotic Plaque, Proceedings of IEEE Computers in Cardiology, 791–794; Lee et al. (1996), Circumferential Stress and Matrix Metalloproteinase 1 in Human Coronary Atherosclerosis: Implications for Plaque Rupture, Atherosclerosis Thrombosis Vascular Biology, 16, 1070–1073; Vonesh et al. (1997), Regional Vascular Mechanical Properties by 3-D Intravascular Ultrasound Finite-Element Analysis, American Journal of Physiology, 272, 425–437; Beattie et al. (1999), Mechanical Modeling: Assessing Atherosclerotic Plaque Behavior and Stability in Humans, International Journal of Cardiovascular Medical Science, 2(2), 69–81; and Feezor et al. (2001), Integration of Animal and Human Coronary Tissue Testing with Finite Element Techniques for Assessing Differences in Arterial Behavior, BED-Vol. 50, 2001 Bioengineering Conference, ASME 2001. Further, these studies have indicated that such high stress regions correlate with the observed prevalence of locations of cap fracture. Moreover, it has been shown that subintimal structural features such as the thickness of the fibrous cap and the extent of the lipid core, rather than stenosis severity are critical in determining the vulnerability of the plaque. The rupture of a highly stressed fibrous cap can be prevented by using novel, interventional, therapeutic techniques such as specially designed stents that redistribute and lower the stresses in the fibrous cap.

One of the avenues to reduce cap rupture is to reinforce the strength and increase thickness of the fibrous cap. Studies have shown that placement of the intravascular stent at a lesion site can induce neointimal thickening. Using the same reasoning, placing an intravascular stent at the vulnerable plaque site can induce neointimal thickening, which in turn will increase the cap thickness. However, a special stent pattern, rather than the traditional workhorse stent, should be used to stent these lesions. A pattern which induces less shear stress upon expansion, less point stress upon the vessel wall and delayed neointimal thickening should be used for stent vulnerable plaques.

Stents are generally tubular-shaped devices which function to hold open a segment of a blood vessel, coronary artery, or other body lumen. They are particularly suitable for use to support and hold back a dissected arterial lining which can occlude the fluid passageway therethrough.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior art stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility, in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, again all of the component parts being formed from the same polymer material. These types of stents, the ones formed from a metal and the ones formed from a polymer, each have advantages and disadvantages. One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels, however, such polymer stents may lack the radial strength necessary to adequately support the lumen once implanted into an occlusive fibromuscular lesion of 70% stenosis or greater.

What has been needed and heretofore unavailable is a stent that can be used to treat a vulnerable plaque by reducing the cap stresses. The present invention satisfies this need and others.

SUMMARY OF THE INVENTION

The present invention is directed to an intravascular stent assembly that can be used to treat a lesion with vulnerable plaque by reducing the cap stresses. The invention also includes methods of using the stent assembly for the treatment of the same.

The stent assembly embodying features of the invention can be readily delivered to the desired body lumen, such as a coronary artery (peripheral vessels, bile ducts, etc.), by mounting the stent assembly on an expandable member of a delivery catheter, for example a balloon, and advancing the catheter and stent assembly through the body lumen to the target site. Generally, the stent is compressed or crimped onto the balloon portion of the catheter so that the stent assembly does not move longitudinally relative to the balloon portion of the catheter during delivery through the arteries, and during expansion of the stent at the target site. The stent is relatively flexible along its longitudinal axis to facilitate delivery through tortuous body lumens yet is stiff and stable enough radially in an expanded condition to maintain the patency of a body lumen such as an artery when implanted therein.

In one embodiment, the stent assembly of the invention includes a series of cylindrical rings formed with undulations and located within distal, center, and proximal sections of the stent. The undulations of the rings located in the center section may have either smaller or larger cross-sectional widths than the undulations of the rings in the distal and proximal sections in order to accommodate the vulnerable plaque section of the artery. Links are incorporated to connect all the cylindrical rings together into the stent assembly. The center section may also be coated with a polymer to increase surface area.

In another embodiment, the stent assembly of the present invention includes a series of cylindrical rings with undulations and also located within distal, center, and proximal sections of the stent. Similarly, the undulations of the rings located in the center section may have either smaller or larger cross-sections than the undulations of the rings in the distal and proximal sections in order to accommodate the vulnerable plaque section of the artery. The rings are directly connected to each other, generally without the need for separate links. The center section may also be coated with a polymer to increase surface area.

The resulting stent structures are a series of radially expandable cylindrical rings which are configured so that vulnerable plaque and small dissections in the wall of a body lumen may be pressed back into position against the luminal wall, while maintaining the longitudinal flexibility of the stent both when being negotiated through the body lumens in their unexpanded state and when expanded into position. The rings within the center section are arranged to provide the section with a high surface area density to reduce the likelihood of plaque rupture by creating less stress on the plaque. The high surface area also helps to reduce the scissoring affect the center section rings may have upon expansion. Undulations within the cylindrical rings allow for an even expansion around the circumference by accounting for the relative differences in stress created by the radial expansion of the cylindrical rings. Each of the individual cylindrical rings may rotate slightly relative to their adjacent cylindrical rings without significant deformation, cumulatively providing stents which are flexible along their length and about their longitudinal axis, but which are still very stable in the radial direction in order to resist collapse after expansion.

Each of the embodiments of the invention can be readily delivered to the desired luminal location by mounting them on an expandable member of a delivery catheter, for example a balloon, and passing the catheter-stent assembly through the body lumen to the implantation site. A variety of means for securing the stents to the expandable member on the catheter for delivery to the desired location is available. It is presently preferred to compress the stent onto the unexpanded balloon. Other means to secure the stent to the balloon include providing ridges or collars on the inflatable member to restrain lateral movement, using bioabsorbable temporary adhesives, or a retractable sheath to cover the stent during delivery through a body lumen.

The presently preferred structures for the expandable cylindrical rings which form the stents of the present invention generally have a plurality of circumferential undulations containing a plurality of alternating peaks and valleys. The peaks and valleys are formed in generally U- and V-shaped patterns and aligned along the longitudinal axis.

While the cylindrical rings and links generally are not separate structures, they have been conveniently referred to as rings and links for ease of identification. Further, the cylindrical rings can be thought of as comprising a series of U-and V-shaped structures in a repeating pattern. While the cylindrical rings are not divided up or segmented into U's and V's, the pattern of cylindrical rings resemble such configuration. The U's and V's promote flexibility in the stent primarily by flexing and may tip radially outwardly as the stent is delivered through a tortuous vessel.

The undulations of the cylindrical rings can have different degrees of curvature and angles of adjacent peaks and valleys to compensate for the expansive properties of the peaks and valleys. The cylindrical rings of the stents are plastically deformed when expanded (except with NiTi alloys) so that the stents will remain in the expanded condition and therefore they must be sufficiently rigid when expanded to prevent the collapse thereof in use.

With stents formed from super-elastic nickel-titanium (NiTi) alloys, the expansion occurs when the stress of compression is removed. This allows the phase transformation from martensite back to austenite to occur, and as a result the stent expands.

After the stents are expanded some of the peaks and/or valleys may, but not necessarily, tip outwardly and embed in the vessel wall. Thus, after expansion, the stents may not have a smooth outer wall surface, rather they have small projections which embed in the vessel wall and aid in retaining the stents in place in the vessel.

The links which interconnect adjacent cylindrical rings can have a cross-section similar to the cross-sections of the undulating components of the expandable cylindrical rings. The links may be formed in a unitary structure with the expandable cylindrical rings formed from the same intermediate product, such as a tubular element, or they may be formed independently and mechanically secured between the expandable cylindrical rings. The links may be formed substantially straight or with a plurality of undulations. They may also be used primarily to support the vulnerable plaque region or primarily to connect adjacent rings.

Preferably, the number, shape and location of the links can be varied in order to develop the desired vulnerable plaque coverage and longitudinal flexibility. These properties are important to minimize alteration of the natural physiology of the body lumen into which the stent is implanted and to maintain the compliance of the body lumen which is internally supported by the stent. Generally, the greater the longitudinal flexibility of the stents, the easier and the more safely they can be delivered to the implantation site, especially where the implantation site is on a curved section of a body lumen, such as a coronary artery or a peripheral blood vessel, and especially saphenous veins and larger vessels.

The stent may be formed from a tube by laser cutting the pattern of cylindrical rings and undulating links in the tube, by individually forming wire rings and laser welding them together, and by laser cutting a flat metal sheet in the pattern of the cylindrical rings and links, and then rolling the pattern into the shape of the tubular stent and providing a longitudinal weld to form the stent.

Other features and advantages of the present invention will become more apparent from the following detailed description of the invention, when taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged or diseased artery.

FIG. 3 is an elevational view, partially in section, depicting the expanded stent within the artery after withdrawal of the delivery catheter.

DETAILED DESCRIPTION OF THE PREFERRED EMBODIMENTS

Figure 4:
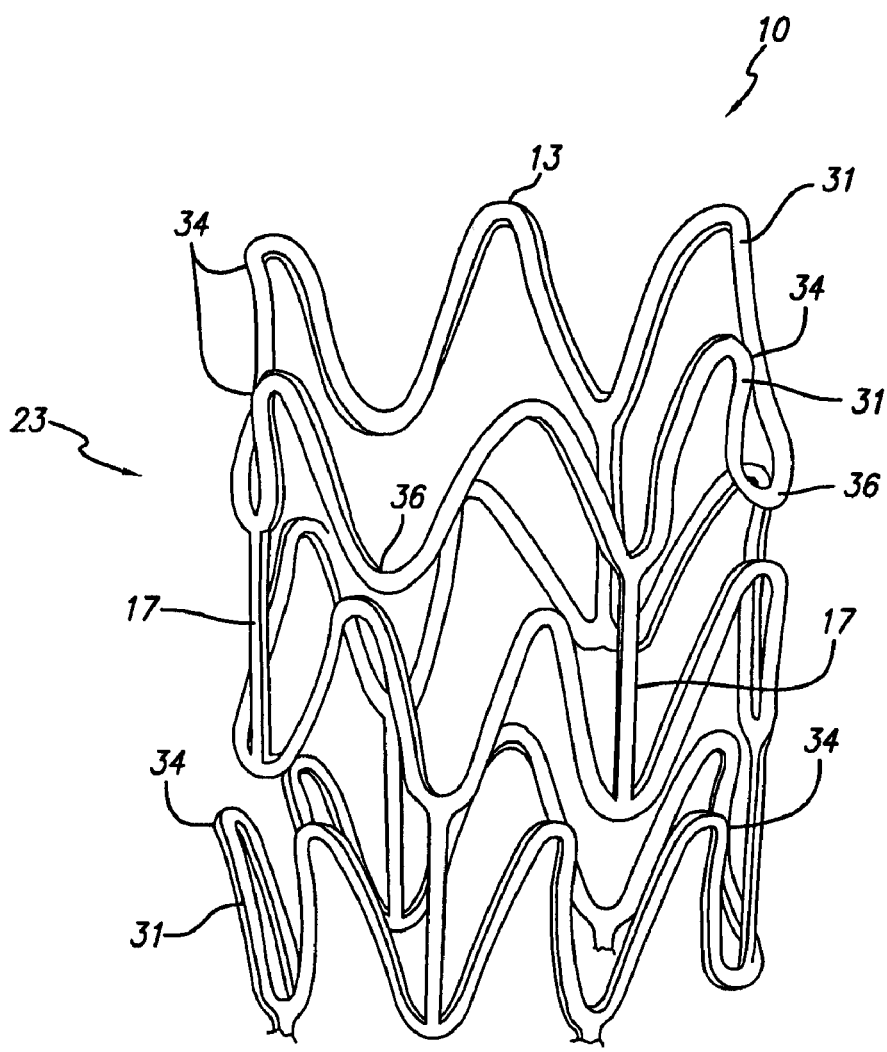
FIG. 4 is a perspective view of the center section of the stent of FIG. 3 in its expanded state depicting the serpentine pattern along the peaks and valleys that form the cylindrical rings.

Before describing in detail an exemplary embodiment of a stent for the treatment of a vulnerable plaque in accordance with the present invention, it is instructive to briefly describe a typical stent implantation procedure and the vascular conditions which are typically treated with stents.

Turning to the drawings, FIG. 1 depicts a metallic stent 10 incorporating features of the invention mounted on a catheter assembly 12 which is used to deliver the stent and implant it in a body lumen, such as a coronary artery, peripheral artery, or other vessel or lumen within the body. The stent generally includes a plurality of radially expandable cylindrical rings 11,13 disposed generally coaxially and interconnected by undulating links 15 and straight links 17 disposed between adjacent cylindrical rings. The stent as shown in FIG. 2 generally includes distal 21, center 23, and proximal 25 sections. The catheter assembly shown in FIG. 1 includes a catheter shaft 13 which has a proximal end 14 and a distal end 16. The catheter assembly is configured to advance through the patient's vascular system by advancing over a guide wire by any of the well known methods of an over the wire (OTW) system (not shown) or a well known rapid exchange (RX) catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire exits the catheter distal end 16 so that the catheter advances along the guide wire on a section of the catheter between the RX port and the catheter distal end. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque 27 that has been previously treated by an angioplasty or other repair procedure. Stent assembly 10 of the present invention is used to repair a diseased or damaged arterial wall which may include the plaque as shown in FIG. 1, or a dissection, or a flap which are commonly found in the coronary arteries, peripheral arteries and other vessels.

In a typical procedure to implant stent assembly 10, the guide wire 18 is advanced through the patient's vascular system by well known methods so that the distal end of the guide wire is advanced past the plaque or diseased area 26. Prior to implanting the stent assembly, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent assembly is positioned in the target area. The expandable member or balloon 22 is inflated by well known means so that it expands radially outwardly and in turn expands the stent assembly radially outwardly until the stent assembly is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIG. 2, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The rings 11,13 and links 15,17 of the stent will eventually become endothelialized. It is this endothelialization and subsequent neointimal growth that will integrate the device into the fibrous cap portion of the vulnerable plaque along with the remainder of the stented portion of the artery. This integration will yield lower fibrous cap stresses overall. The undulating portion of the stent provides good tacking characteristics to prevent stent movement within the artery. Furthermore, the closely spaced cylindrical rings at regular intervals provide uniform support for the wall of the artery, and consequently are well adapted to tack up and hold in place small flaps or dissections in the wall of the artery.

The stent patterns shown in FIGS. 1–3 are for illustration purposes only and can vary in size and shape to accommodate different vessels or body lumens. Further, the stent 10 is of a type that can be used in accordance with the present invention.

The first set of links and second set of links 15,17 which interconnect adjacent first sets of cylindrical rings and adjacent second sets of cylindrical rings 11,13 may have radial cross-sections similar to the radial cross-sections of the undulating components of either set of expandable cylindrical rings. In one embodiment, all of the links are joined at either the peaks or the valleys of the undulating structure of adjacent cylindrical rings. In this manner there is little or no shortening of the stent assembly upon expansion.

The number and location of the first set of links and the second set of links 15,17 connecting the first set of rings and second set of rings 11,13 can be varied in order to vary the desired longitudinal and flexural flexibility in the stent assembly structure both in the unexpanded as well as the expanded condition. These properties are important to minimize alteration of the natural physiology of the body lumen into which the stent assembly is implanted and to maintain the compliance of the body lumen which is internally supported by the stent assembly. Generally, the greater the longitudinal and flexural flexibility of the stent assembly, the easier and the more safely it can be delivered to the target site.

With reference to FIG. 4, which illustrates the center section 23 of the stent 10, the cylindrical rings 13 are in the form of undulating portions. The undulating portion is made up of a plurality of V-shaped members 31 having radii that more evenly distribute expansion forces over the various members. After the cylindrical rings have been radially expanded, outwardly projecting edges 34,36 may be formed. That is, during radial expansion some of the V-shaped members may tip radially outwardly thereby forming outwardly projecting edges. These outwardly projecting edges can provide for a roughened outer wall surface of the stent and assist in implanting the stent in the vascular wall by embedding into the vascular wall. In other words, the outwardly projecting edges may embed into the vascular wall, for example arterial vessel 24, as depicted in FIG. 3. Depending upon the dimensions of the stent and the thickness of the various members making up the serpentine pattern, any of the V-shaped members can tip radially outwardly to form the projecting edges. The rings within the distal section and proximal section 21,25 of the stent can be configured similarly to tip outwardly.

Cylindrical rings 13 can be nested such that adjacent rings slightly overlap in the longitudinal direction so that one ring is slightly nested within the next ring and so on. The degree of nesting can be dictated primarily by the length of each cylindrical ring, the number of undulations in the rings, the thickness of the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings may be slightly nested even after the stent is expanded, which enhances vessel wall coverage. In some circumstances, it may not be desirable to nest one ring within the other, which is also contemplated by the invention. As mentioned above, the distal section and proximal section 21,25 can be configured similarly.

Figure 5:
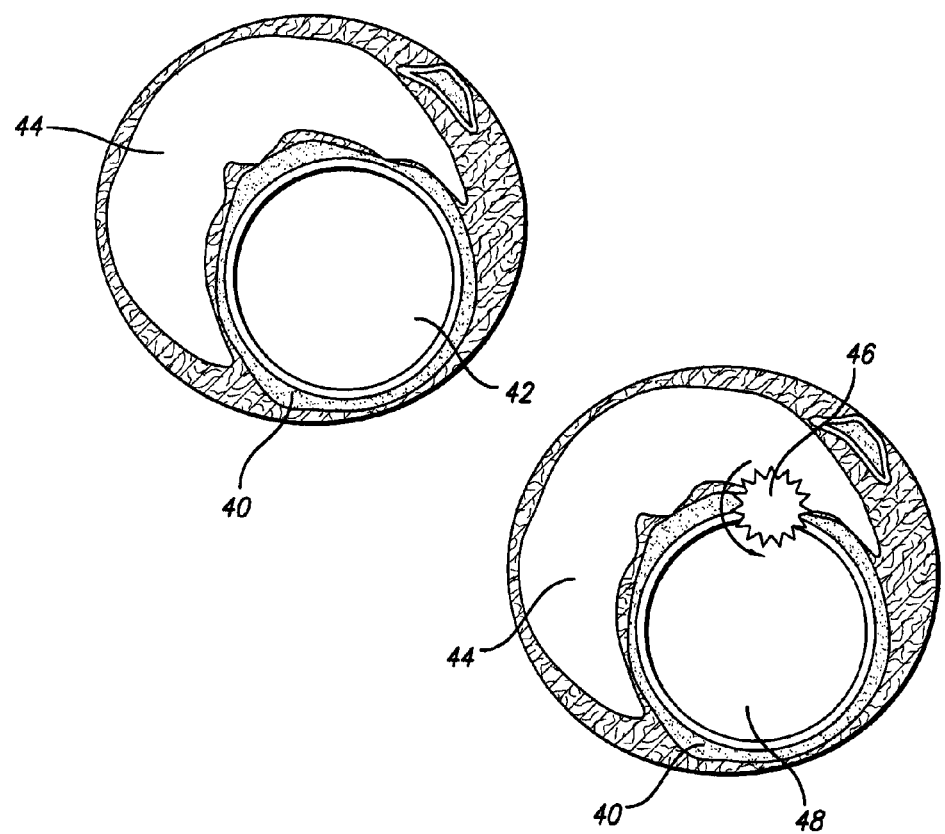
FIG. 5 is a schematic of a process of fibrous cap rupture in a fibroatheroma form of vulnerable plaque leading to a thrombotic occlusion of an artery.

FIG. 5 illustrates a schematic of a process of fibrous cap rupture in a fibroatheroma form of vulnerable plaque leading to a thrombotic occlusion of an artery 24 (FIG. 1). A patent lumen 42 at the lesion site is separated from a lipid core 44 of the lesion by the fibrous cap 40. When the fibrous cap is ruptured 46, the lumenal blood becomes exposed to tissue factor, a highly thrombogenic core material, which can result in total thrombotic occlusion 48 of the artery. The intravascular stent assembly of the present invention is a novel, interventional, therapeutic technique that redistributes and lowers the stresses in the fibrous cap.

Figure 6:
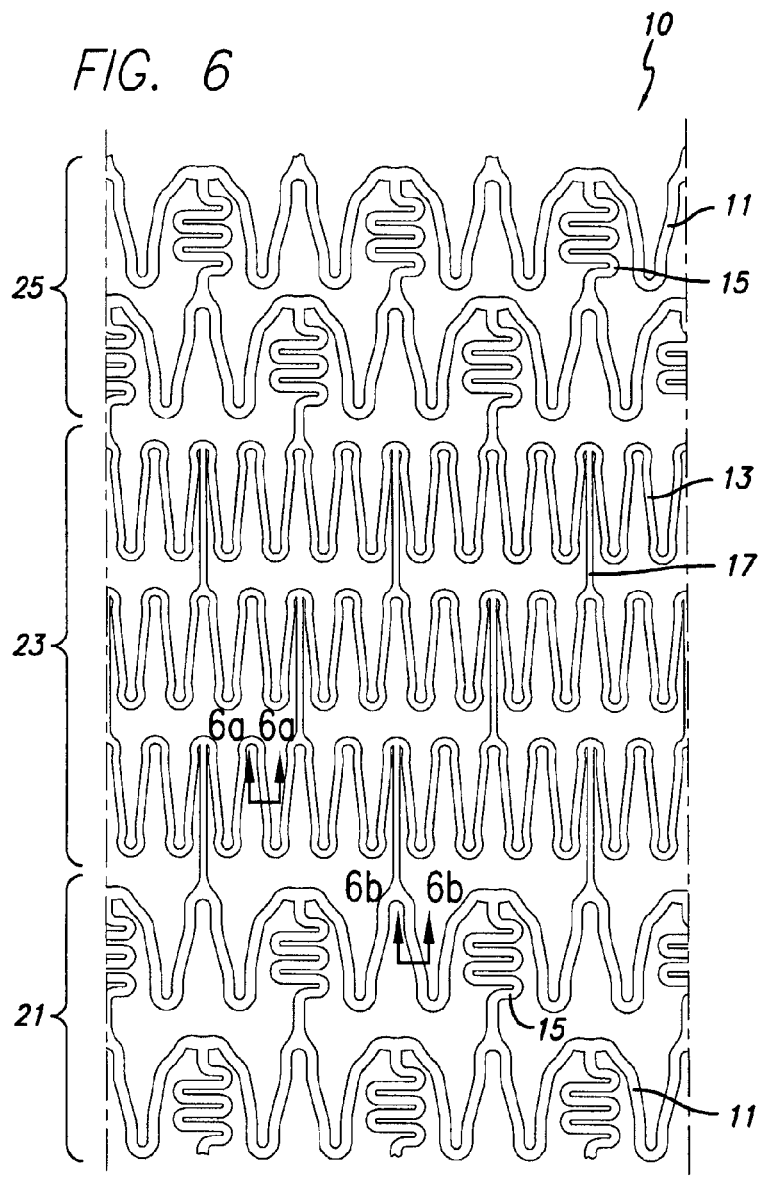
FIG. 6 is a plan view of a flattened section of one embodiment of a stent of the invention including undulating links and U- and V-shaped ring undulations.
Figure 6A:
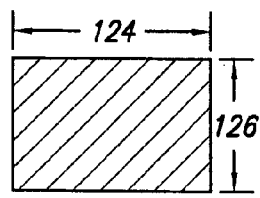
FIG. 6a is a cross-sectional view of an undulation within a center ring taken along line 6a—6a of FIG. 6.
Figure 6B:
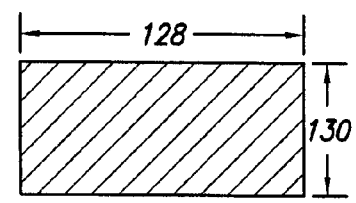
FIG. 6b is a cross-sectional view of an undulation within a distal ring taken along line 6b—6b of FIG. 6.

In one embodiment shown in FIG. 6, the stent assembly 10 of the present invention has a plurality of a first set and second set 11,13 of flexible undulating cylindrical rings being expandable in a radial direction, with each of the rings having a first delivery diameter and a second implanted diameter and being aligned on a common longitudinal axis. The undulations within the first set of rings have a radial cross-section shown in FIG. 6b with a width 128 and height 130. The first set of links have a similar radial cross-section. At least one first set link 15 is attached between adjacent first set rings to form the distal section and proximal section 21,25 of the stent. The first set of links are formed with W-shaped undulations which add to the stent's flexibility. Preferably, each of the rings is formed of a metallic material. However, the stent assembly of the present invention is not limited to the use of such metallic materials as non-metallic materials are also contemplated for use with the invention. The center section 23 has a plurality of a second set of rings with V-shaped undulations 13 and a second set of substantially straight links 17. The undulations within the second set of rings have a radial cross-section shown in FIG. 6a with a width 124 and height 126. The second set of links have a similar radial cross-section. The length of a characteristic vulnerable plaque region is generally in the range of about 3 to 30 mm, and it is preferable that the length of the center section is slightly longer than the vulnerable plaque region. In any event, the center section should be long enough to cover the vulnerable plaque region. Thus, for some applications, the center section may be longer or shorter than the disclosed range. The center section can be fabricated in a multiplicity of sizes in order to accommodate multiple lengths of lesions containing vulnerable plaque that require treatment. The width 124 of the links and the undulations within the rings in the center section is smaller than the width 128 of the links and the undulations in the rings in the distal and proximal sections and can vary depending on the severity of vulnerable plaque to be treated.

The stent assembly of the present invention is placed in an artherosclerotic artery such that upon deployment the center section 23 apposes the region containing the vulnerable plaque. With further reference to FIG. 6, the center section 23 of the stent assembly apposes the treatment site (not shown) within the body lumen while the rings are in the implanted diameter (FIG. 3). This configuration could be applicable for at least two reasons. First, given that pervious studies have suggested that many vulnerable plaques are not occlusive prior to the thrombotic event, these plaques could require less scaffolding strength than typical metallic stents are designed to provide. Second, in the event of cap rupture within the plaque, the dense center section could provide high coverage and focal drug delivery to the rupture region. For purposes of this invention, the treatment site is preferably an artery 24 having at least one lesion containing vulnerable plaque 27 (FIG. 1).

Figure 7:
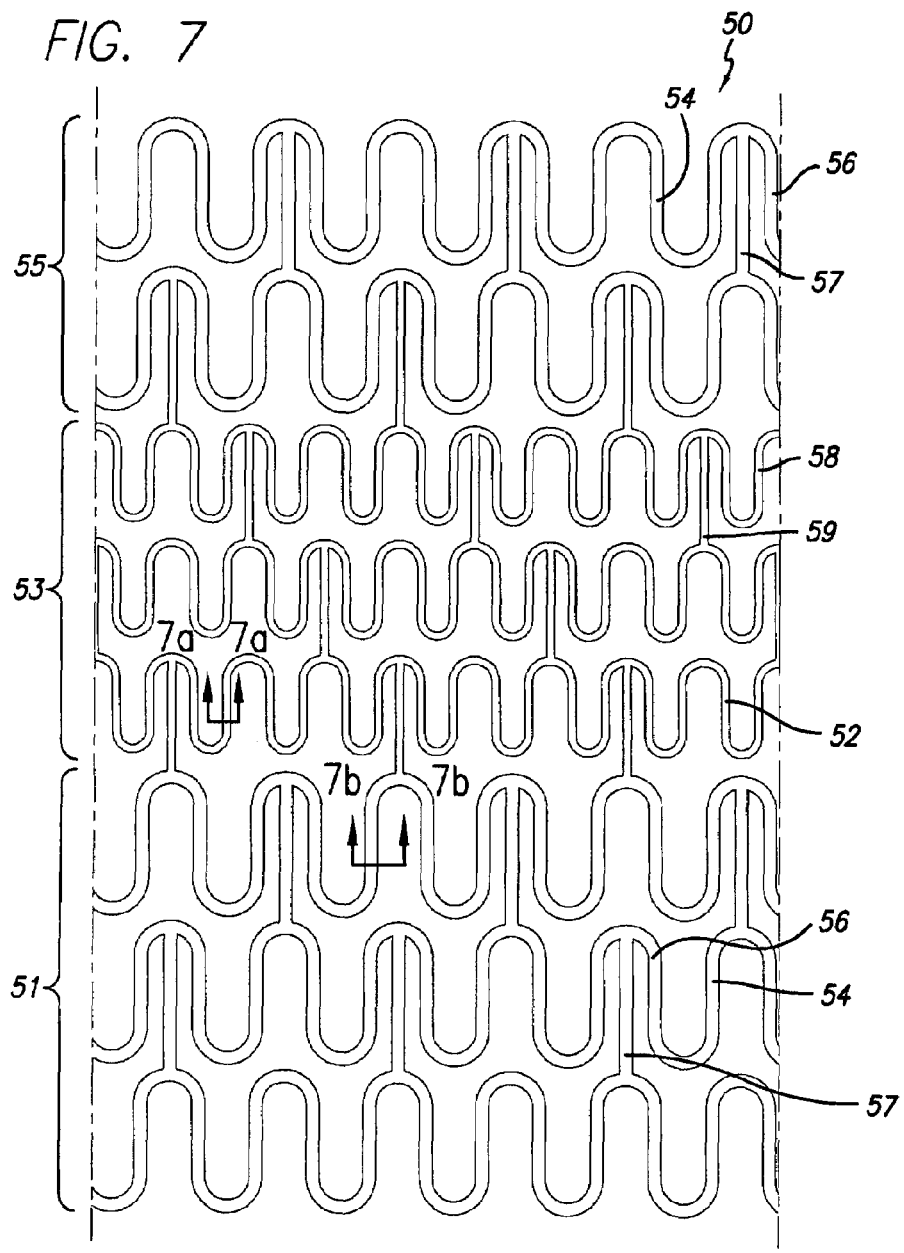
FIG. 7 is a plan view of a flattened section of one embodiment of a stent of the invention including two sets of rings, each with U-shaped undulations.

The stent 50 shown in FIG. 7 includes a distal section 51, center section 53, and proximal section 55. A first set of rings 56 with undulations having a first radial cross-section shown in FIG. 7b with a width 136 and height 138 and a first set of substantially straight links 57 also with a similar radial cross-section are located within the distal and proximal sections. The links connect adjacent rings in both sections.

Figure 7A:
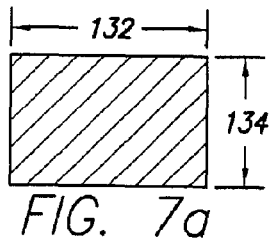
FIG. 7a is a cross-sectional view of an undulation within a center ring taken along line 7a—7a of FIG. 7.
Figure 7B:
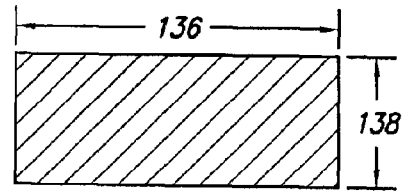
FIG. 7b is a cross-sectional view of an undulation within a distal ring taken along line 7b—7b of FIG. 7.

The center section 53 includes a second set of rings 58 with undulations having a second, relatively smaller radial cross-section shown in FIG. 7a with a width 132 and height 134 and a second set of substantially straight links 59 with a similar radial cross-section connecting adjacent rings. The undulations 52 of the three center section rings are substantially U-shaped and have a smaller radial cross-sectional width 132 than the width 136 of the U-shaped undulations 54 in the first set of rings. In addition, the second set of links are shorter than the first set of distal and proximal links 57 and also have a smaller radial cross-sectional width 132. The smaller dimensions and higher undulation concentrations of the second set of rings and links helps to redistribute and lower stresses in the fibrous cap of the artery.

Figure 8:
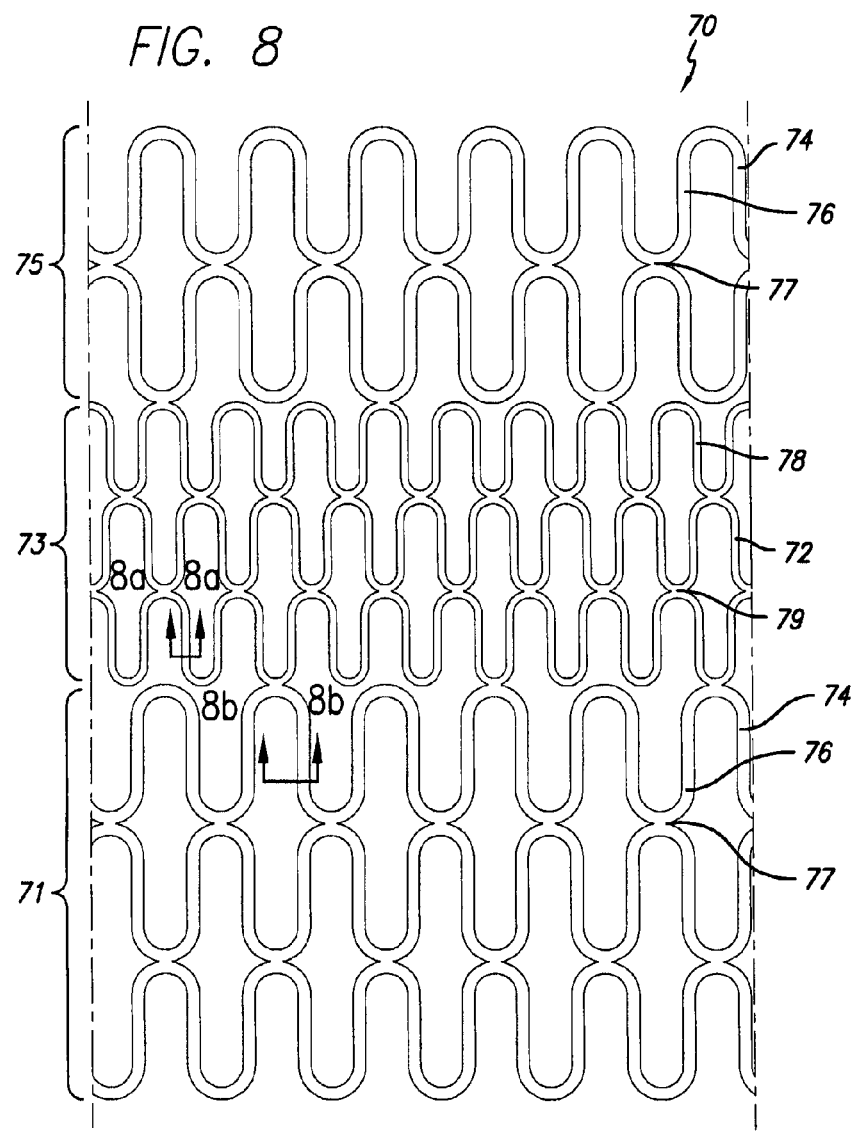
FIG. 8 is a plan view of a flattened section of one embodiment of a stent of the invention including two sets of rings with U-shaped undulations where the rings are directly connected to each other.

The stent 70 shown in FIG. 8 also includes a distal section 71, center section 73, and proximal section 75. A first set of rings 76 with undulations having a first radial cross-section shown in FIG. 8b with a width 144 and height 146 are located within the distal and proximal sections. Adjacent rings in both sections are directly connected through attachment points 77.

Figure 8A:
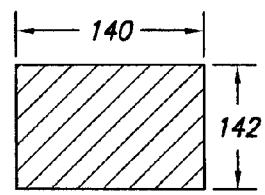
FIG. 8a is a cross-sectional view of an undulation within a center ring taken along line 8a—8a of FIG. 8.
Figure 8B:
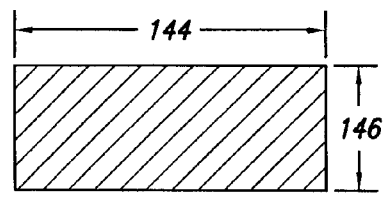
FIG. 8b is a cross-sectional view of an undulation within a distal ring taken along line 8b—8b of FIG. 8.

The center section 73 includes a second set of rings 78 with undulations having a second, smaller radial cross-section shown in FIG. 8a with a width 140 and height 142. Like the distal section 71 and proximal section 75, adjacent rings in the center section are directly connected through attachment points 79. Similar to FIG. 7, the undulations 72 of the center section are substantially U-shaped and the rings incorporate more undulations per ring and the undulations have a smaller radial cross-sectional width 140 than the width 144 of the rings within the distal and proximal sections, also with U-shaped undulations 74. As in FIG. 7, the smaller dimensions of the second set of rings helps to redistribute and lower stresses in the fibrous cap.

Figure 9:
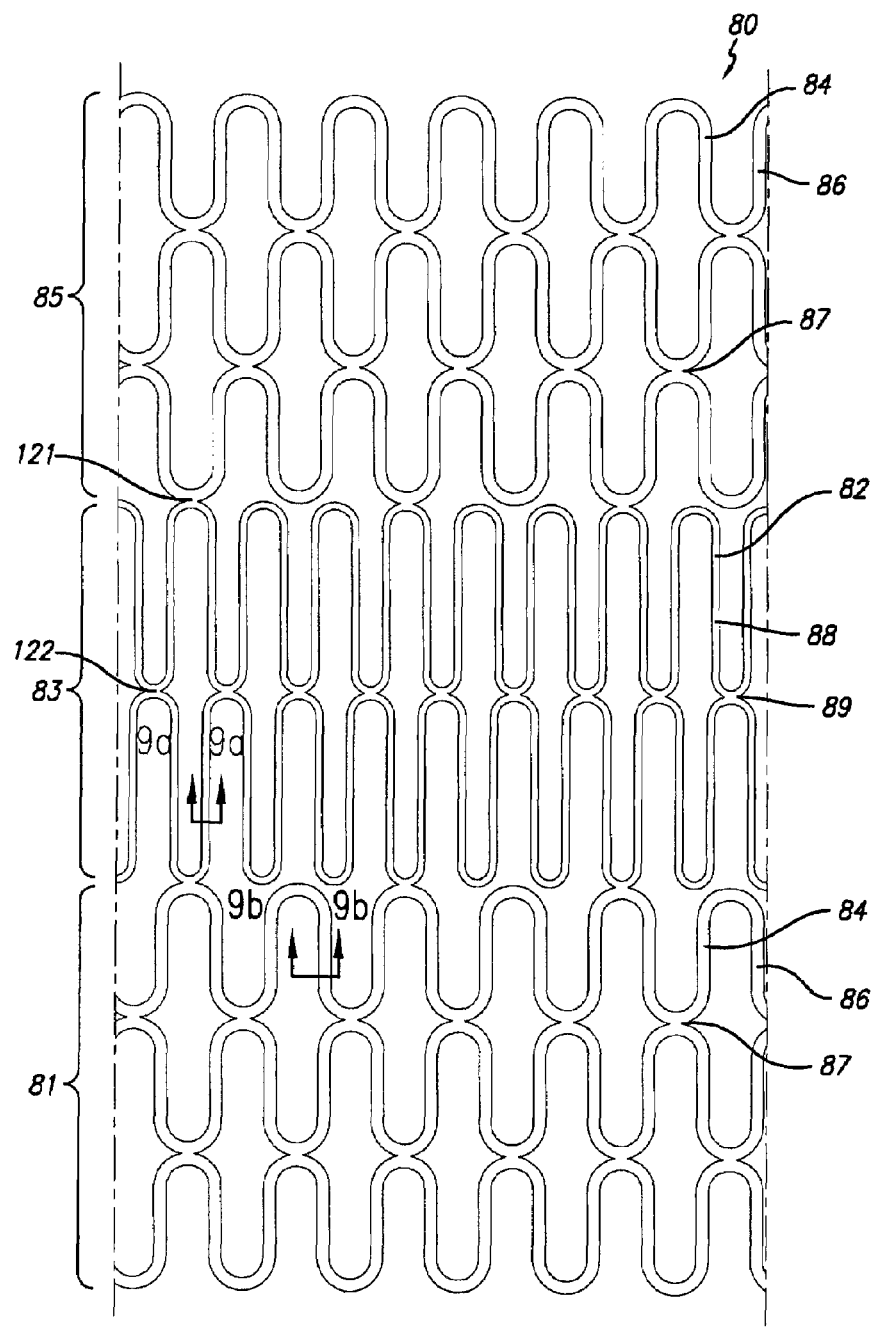
FIG. 9 is a plan view of a flattened section of one embodiment of a stent of the invention including two sets of rings with U-shaped undulations where a center set consists of two rings.

The stent 80 shown in FIG. 9 also includes distal section 81, center section 83, and proximal section 85. A first set of rings 86 with undulations having a first radial cross-section shown in FIG. 9b with a width 152 and height 154 and located within the distal and proximal sections. Adjacent rings in both sections are directly connected through attachment points 87.

Figure 9A:
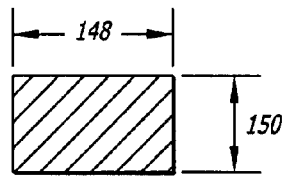
FIG. 9a is a cross-sectional view of an undulation within a center ring taken along line 9a—9a of FIG. 9.
Figure 9B:
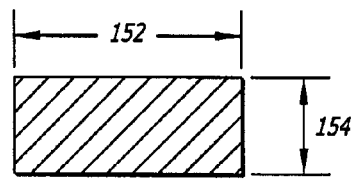
FIG. 9b is a cross-sectional view of an undulation within a distal ring taken along line 9b—9b of FIG. 9.

The center section 83 includes a second set of rings 88 with undulations having a second, smaller radial cross-section shown in FIG. 9a with a width 148 and height 150. Like the distal section 81 and proximal section 85, adjacent rings in the center section are directly connected through attachment points 89. Similar to FIGS. 7 and 8, the undulations 82 of the center section are substantially U-shaped and the rings have more undulations per ring and the undulations have a smaller cross-sectional width 148 that the width 152 of the first set of rings 86 located within the distal and proximal sections, also with U-shaped undulations 84. The second set of rings are also longer from peak 121 to valley 122 than the first set of rings. The increase in length helps flexibility within the center section. As in FIGS. 7 and 8, the relatively smaller radial cross-sectional width 148 and larger number of U-shaped undulations within the center section help to redistribute and lower stresses in the fibrous cap.

Figure 10:
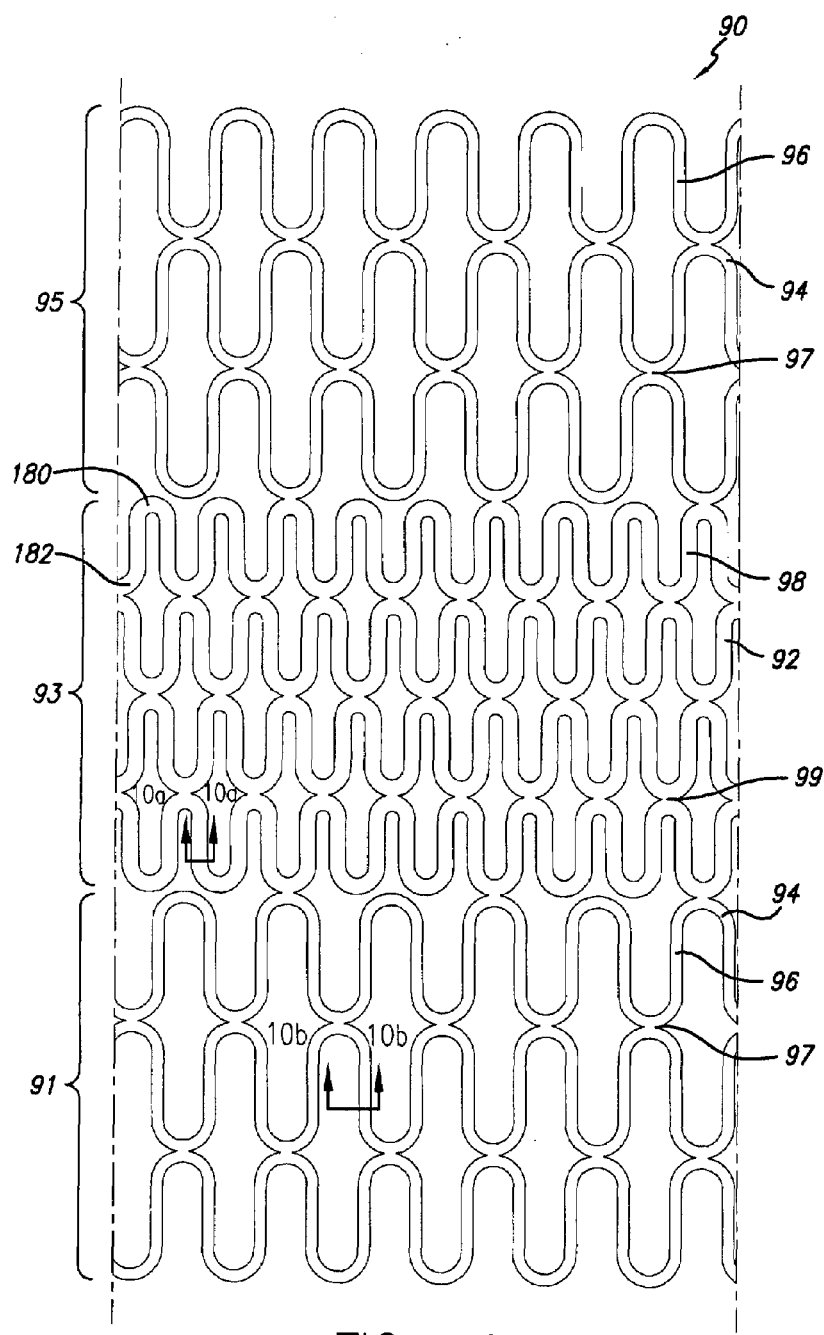
FIG. 10 is a plan view of a flattened section of one embodiment of a stent of the invention including a center set consisting of four rings.

The stent 90 shown in FIG. 10 includes a distal section 91, center section 93, and proximal section 95. A first set of rings 96 are located within the distal and proximal sections, the rings having undulations with a first radial cross-section shown in FIG. 10b with a width 160 and height 162. Adjacent rings in both sections are directly connected through attachment points 97.

Figure 10A:
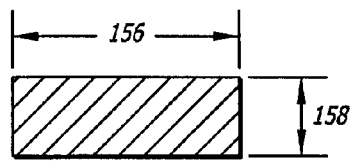
FIG. 10a is a cross-sectional view of an undulation within a center ring taken along line 10a—10a of FIG. 10.
Figure 10B:
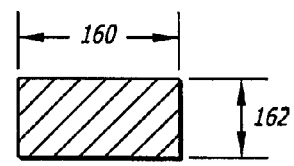
FIG. 10b is a cross-sectional view of an undulation within a distal ring taken along line 10b—10b of FIG. 10.

The center section 93 includes a second set of rings 98 with undulations having a second, wider radial cross-section shown in FIG. 10a with a width 156 and height 158. Like the distal section 91 and proximal section 95, adjacent rings in the center section are directly connected through attachment points 99. The undulations 92 of the center section are substantially U-shaped and the rings incorporate more undulations per ring and are shorter from peak 180 to valley 182 than the distal and proximal rings 96, which also incorporate U-shaped undulations 94. When compared to the stent shown in FIG. 8, the stent of FIG. 10, allows a greater fibrous cap coverage area due to the higher number of second set rings and due to the larger radial ring cross-sectional width 156.

Figure 11:
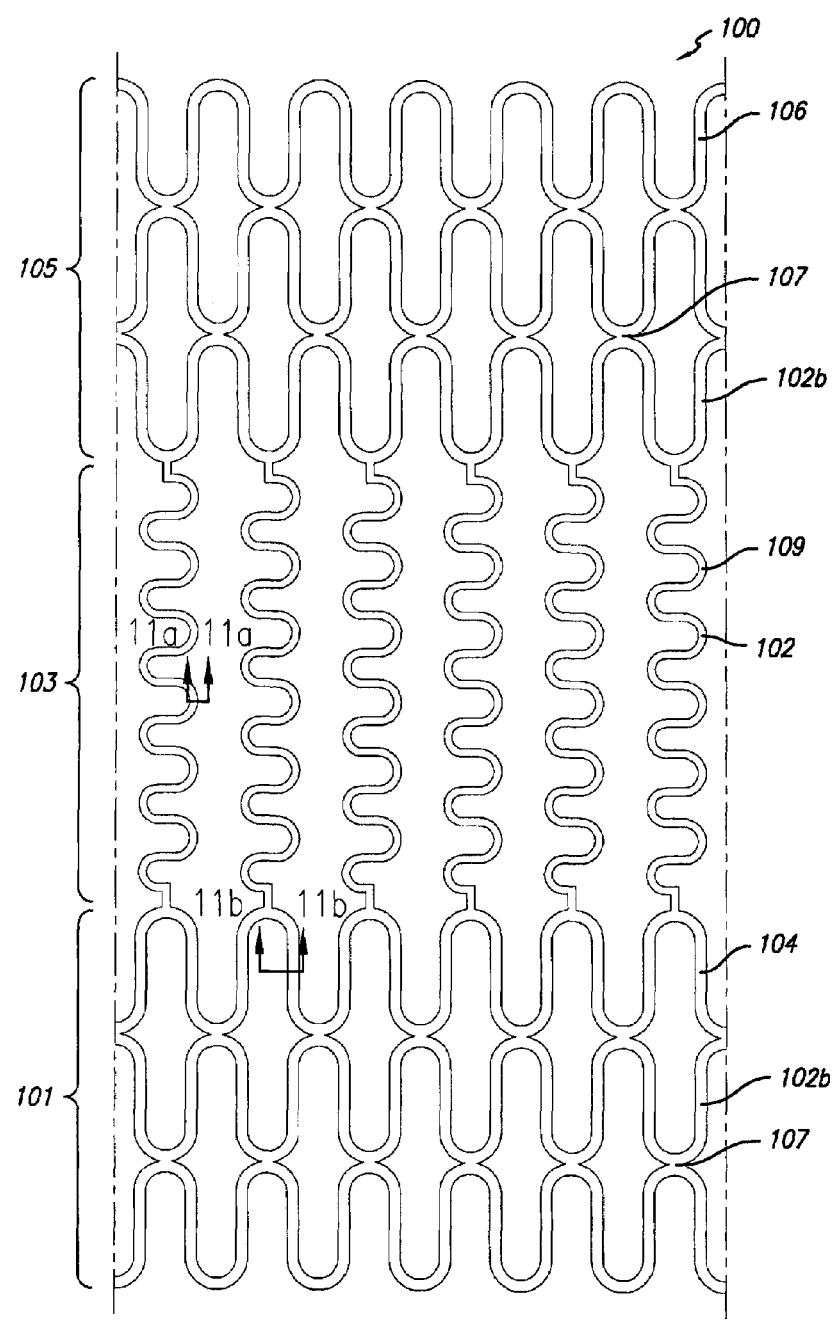
FIG. 11 is a plan view of a flattened section of one embodiment of a stent of the invention including six links within a center section.
Figure 11A:
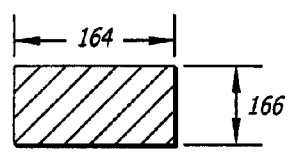
FIG. 11a is a cross-sectional view of an undulation within a center link taken along line 11a—11a of FIG. 11.
Figure 11B:
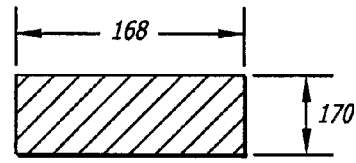
FIG. 11b is a cross-sectional view of an undulation within a distal ring taken along line 11b—11b of FIG. 11.

The stent 100 shown in FIG. 11 also includes a distal section 101, center section 103, and proximal section 105. A first set of rings 106 are located within the proximal section and a second set of rings 104 are located within the distal section, each set of rings with undulations having a first radial cross-section shown in FIG. 11b with a width 168 and height 170. Adjacent rings in both sections are directly connected through attachment points 107. In this particular embodiment, the first and second set of rings are identically configured and share the same cross-section shown in FIG. 11b.

The center section 103 differs from previous embodiments because it incorporates a series of six links 109 to cover the fibrous cap of an artery. The links incorporate U-shaped undulations 102 which are arranged perpendicular to the stent longitudinal axis and connect to the U-shaped undulations 102b within the rings 104,106. The undulations 102 allow the links to cover more surface area and have greater flexibility than would a similar straight link. The links also incorporate a radial cross-section shown in FIG. 11a with a relatively smaller width 164 and height 166 for added flexibility.

Figure 12:
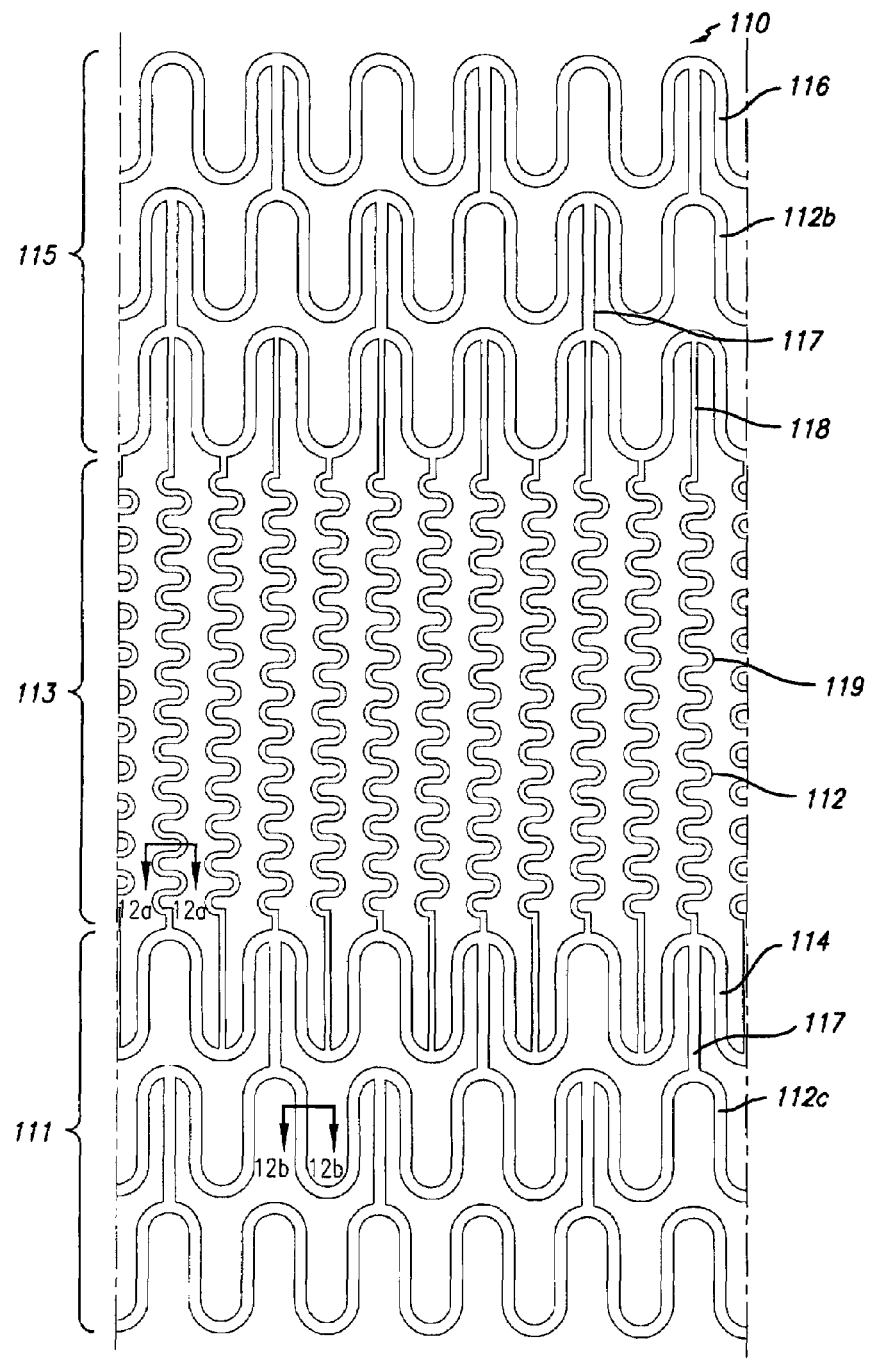
FIG. 12 is a plan view of a flattened section of one embodiment of a stent of the invention including twelve links within a center section.

The stent 110 shown in FIG. 12 also includes a distal section 111, center section 113, and proximal section 115. Similar to FIG. 11, a series of links 119 form the center section of the stent of the present embodiment.

Figure 12A:
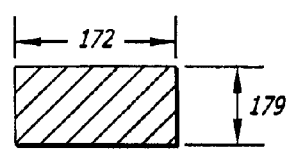
FIG. 12a is a cross-sectional view of an undulation within a center link taken along line 12a—12a of FIG. 12.
Figure 12B:
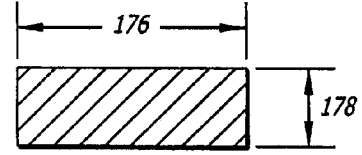
FIG. 12b is a cross-sectional view of an undulation within a distal ring taken along line 12b—12b of FIG. 12.

A first set of undulating rings 116 located within the proximal section and a second set of undulating rings 114 are located with the distal section, each with undulations having a first radial cross-section shown in FIG. 12b with a width 176 and height 178. Adjacent rings in both sections are directly connected through a first set of links 117. In this particular embodiment, the first and second set of rings are identically configured and share the same radial cross-section shown in FIG. 12b. The first set of links are configured with a radial cross-section identical to the rings.

The center section 113 incorporates a second set of twelve links 119 to cover the fibrous cap of an artery. The second set of links, like the links 109 shown in FIG. 11, incorporate U-shaped undulations 112 which are arranged perpendicular to the stent longitudinal axis. The second set of links also incorporate straight portions 118 that fit within the U-shaped undulations 112b,112c of the rings 116,114. The links also incorporate a radial cross-section shown in FIG. 12a with a relatively smaller width 172 and height 179.

The stents of the present invention can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. It is preferred to cut the tubing in the desired pattern by means of a machine-controlled laser, which is well known in the art.

The stent tubing may be made of suitable biocompatible material such as stainless steel, titanium, tungsten, tantalum, vanadium, cobalt chromium, gold, palladium, platinum, and iradium, super-elastic (nickel-titanium) NiTi alloys and even high strength thermoplastic polymers. The stent diameters are very small, so the tubing from which it is made must necessarily also have a small diameter. For PCTA applications, typically the stent has an outer diameter on the order of about 1.65 mm (0.065 inches) in the unexpanded condition, the same outer diameter of the hypotubing from which it is made, and can be expanded to an outer diameter of 5.08 mm (0.2 inches) or more. The wall thickness of the tubing is about 0.076 mm (0.003 inches). For stents implanted in other body lumens, such as PTA applications, the dimensions of the tubing are correspondingly larger. While it is preferred that the stents be made from laser cut tubing, those skilled in the art will realize that the stent can be laser cut from a flat sheet and then rolled up in a cylindrical configuration with the longitudinal edges welded to form a cylindrical member.

In the instance when the stents are made from plastic, the implanted stent may have to be heated within the arterial site where the stents are expanded to facilitate the expansion of the stent. Once expanded, it would then be cooled to retain its expanded state. The stent may be conveniently heated by heating the fluid within the balloon or the balloon itself directly by a known method.

The stents may also be made of materials such as super-elastic (sometimes called pseudo-elastic) nickel-titanium (NiTi) alloys. In this case the stent would be formed full size but deformed (e.g. compressed) to a smaller diameter onto the balloon of the delivery catheter to facilitate intraluminal delivery to a desired intraluminal site. The stress induced by the deformation transforms the stent from an austenite phase to a martensite phase, and upon release of the force when the stent reaches the desired intraluminal location, allows the stent to expand due to the transformation back to the more stable austenite phase. Further details of how NiTi super-elastic alloys operate can be found in U.S. Pat. Nos. 4,665,906 (Jervis) and 5,067,957 (Jervis), incorporated herein by reference in their entirety.

The stent of the invention also can be coated with a drug or therapeutic agent. Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, anti-platelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents are known in the art. Furthermore, the calculation of dosages, dosage rates and appropriate duration of treatment are previously known in the art.

While the invention has been illustrated and described herein in terms of its use as intravascular stents, it will be apparent to those skilled in the art that the stents can be used in other instances in all vessels in the body. Since the stents of the present invention have the novel feature of enhanced longitudinal flexibility, they are particularly well suited for implantation in almost any vessel where such devices are used. This feature, coupled with limited longitudinal contraction of the stent when radially expanded, provides a highly desirable support member for all vessels in the body. Other modifications and improvements may be made without departing from the scope of the invention.

What is claimed:

1. A method for delivering an intravascular stent in an artery having vulnerable plaque, comprising:
    providing an intravascular stent delivery assembly comprising:
    an elongated catheter having an expandable member for expanding a stent and a stent removably mounted on the expandable member where the stent has a distal section with links and rings with both U-shaped and V-shaped undulations, the links and undulations of the distal section having first cross-sectional widths, a proximal section with links and rings with both U-shaped and V-shaped undulations, the links and undulations of the proximal section also having first cross-sectional widths and a center section with links and rings exclusively with non-overlapping V-shaped undulations, the links and undulations of the center section having second, relatively smaller cross-sectional widths and wherein the center section has a higher undulation concentration than said distal and proximal sections;
    advancing the stent delivery assembly into an atherosclerotic artery within the patient's body lumen;
    positioning the stent in the artery such that only the center section of the stent apposes and contacts a region of the artery containing vulnerable plaque;
    inflating the expandable member;
    expanding and implanting the stent in the patient's artery;
    deflating the expandable member; and
    withdrawing the stent delivery catheter assembly from the patient.

2. The method of claim 1, wherein the stent is implanted in the coronary arteries.

3. The method of claim 2, wherein the stent is implanted in the peripheral arteries.

4. The method of claim 1, further comprising identifying an atherosclerotic artery within the patient's body lumen having vulnerable plaque.

5. A method for delivering an intravascular stent in an artery comprising:
    providing an intravascular stent delivery assembly comprising:
    an elongated catheter having an expandable member for expanding a stent and a stent removably mounted on the expandable member where the stent has a distal section with links and rings with a first number of undulations, the links and undulations of the distal section having first cross-sectional widths, a proximal section with links and rings with a first number of undulations, the links and undulations of the proximal section also having first cross-sectional widths and a center section with links and rings with a second number of undulations greater than said first number of undulations, the links and undulations of the center section having second, relatively smaller cross-sectional widths, and the length of the center section is between about 3 mm and about 30 mm, wherein the undulations of the center section are non-overlapping;
    identifying an atherosclerotic artery within the patient's body lumen having vulnerable plaque;
    advancing the stent delivery assembly into the atherosclerotic artery;
    positioning the stent in the artery such that only the center section of the stent apposes and contacts the region of the artery containing vulnerable plaque;
    inflating the expandable member;
    expanding and implanting the stent in the patient's artery;
    deflating the expandable member; and
    withdrawing the stent delivery catheter assembly from the patient.

6. A method for delivering an intravascular stent in an artery having vulnerable plaque, comprising:
    providing an intravascular stent delivery assembly comprising:
    an elongated catheter having an expandable member for expanding a stent and a stent removably mounted on the expandable member where the stent has a distal section, a proximal section, and a center section, each section having links and rings with undulations, wherein the undulations of the center section are non-overlapping and wherein the center section has a higher undulation concentration than the distal section and proximal section so that less stress is effected on the tissue of the artery by the center section than by the distal and proximal sections;

advancing the stent delivery assembly into an atherosclerotic artery within the patient's body lumen;

positioning the stent in the artery such that only the center section of the stent apposes and contacts a region of the artery containing vulnerable plaque;

inflating the expandable member;

expanding and implanting the stent in the patient's artery;

deflating the expandable member; and withdrawing the stent delivery catheter assembly from the patient.

7. A method for delivering an intravascular stent in an artery having vulnerable plaque, comprising:

providing an intravascular stent delivery assembly comprising an elongated catheter having an expandable member for expanding a stent, the stent being removably mounted on the expandable member and having a distal section and a proximal section, both the distal section and the proximal section comprising struts forming rings and links, the struts having first cross-sectional widths, and a center section comprising struts forming rings and links, the struts having second, relatively smaller cross-sectional widths than the first cross-sectional widths, each ring of said center section having a greater number of struts than said rings of said distal and proximal sections, wherein none of the struts of the center section overlap one another;

advancing the stent delivery assembly into an artery within the patient's body lumen;

positioning the stent in the artery such that only the center section of the stent apposes and contacts a region of the artery containing vulnerable plaque;

inflating the expandable member;

expanding and implanting the stent in the patient's artery so that a radial force created by the expanded stent is relatively less in the center section aligned with the vulnerable plaque than in the proximal section and the distal section;

deflating the expandable member; and withdrawing the stent delivery catheter assembly from the patient.

8. The method of claim 7, wherein the center section has a length extending beyond a length of the vulnerable plaque.

9. The method of claim 7, wherein the length of the vulnerable plaque is in the range of about 3 mm (0.118 inch) to about 30 mm (1.1811 inch) and the length of the center section extends beyond the range of lengths of the vulnerable plaque.

10. The method of claim 7, wherein a therapeutic drug is applied to the center section.

* * * * *